US011236076B2

(12) United States Patent
Gallou et al.

(10) Patent No.: US 11,236,076 B2
(45) Date of Patent: Feb. 1, 2022

(54) REACTION MEDIUM CONTAINING WATER-SURFACTANT MIXTURE

(71) Applicant: Novartis AG, Basel (CH)

(72) Inventors: Fabrice Gallou, Basel (CH); Michael Parmentier, Basel (CH); Jianguang Zhou, Changshu/Jiangsu Province (CN); Pengfei Guo, Changshu/Jiangsu Province (CN)

(73) Assignee: Novartis AG, Basel (CH)

( * ) Notice: Subject to any disclaimer, the term of this patent is extended or adjusted under 35 U.S.C. 154(b) by 385 days.

(21) Appl. No.: 16/088,374

(22) PCT Filed: Mar. 27, 2017

(86) PCT No.: PCT/IB2017/051732
§ 371 (c)(1),
(2) Date: Sep. 25, 2018

(87) PCT Pub. No.: WO2017/168303
PCT Pub. Date: Oct. 5, 2017

(65) Prior Publication Data
US 2020/0299281 A1    Sep. 24, 2020

(30) Foreign Application Priority Data

Mar. 29, 2016  (WO) ................ PCT/CN2016/077703

(51) Int. Cl.
| C07D 405/14 | (2006.01) |
| C07C 211/52 | (2006.01) |
| C07C 269/06 | (2006.01) |
| C07D 241/20 | (2006.01) |
| C07D 333/64 | (2006.01) |
| C07D 401/04 | (2006.01) |
| C07D 403/14 | (2006.01) |
| C07D 487/04 | (2006.01) |

(52) U.S. Cl.
CPC .......... *C07D 405/14* (2013.01); *C07C 211/52* (2013.01); *C07C 269/06* (2013.01); *C07D 241/20* (2013.01); *C07D 333/64* (2013.01); *C07D 401/04* (2013.01); *C07D 403/14* (2013.01); *C07D 487/04* (2013.01)

(58) Field of Classification Search
CPC .................................................. C07D 405/14
See application file for complete search history.

(56) References Cited

U.S. PATENT DOCUMENTS 6,479,709 B1    11/2002  Ishikawa

FOREIGN PATENT DOCUMENTS

| DE | 19809166 A1 | 9/1999 |
| JP | 2000239192 A | 9/2000 |
| WO | WO 2011/020900 A2 | 2/2011 |

OTHER PUBLICATIONS

Lipshutz et al., J.nal of Organic Chem. 76(11) 2011 pp. 4379-4391.*
Liu et al., App Organometallic Chem (2013).*
Arcadi et al., Eur. J. Org. Chem (2003) 2003(20) pp. 4080-4086.*
Xin et al., Synthesis (2007) No. 13, pp. 1970-1978.*
Bruce H. Lipshutz et al: "TPGS-750-M : A Second-Generation Amphiphile for Metal-Catalyzed Cross-Couplings in Water at Room Temperature", The Journal of Organic Chemistry, vol. 76, No. 11, Jun. 3, 2011, pp. 4379-4391.
Liu Xiang et al: "The Suzuki cross-coupling reaction in pure water catalyzed by ligandless palladium using polyethylene glycol derivatives as surfactant: The Suzuki cross-coupling reaction in pure water", Applied Organometallic Chemistry, Jul. 1, 2013, pp. 615-618.
Antonio Arcadi et al: "A Mild and Versatile Method for Palladium-Catalyzed Cross-Coupling of Aryl Halides in Water and Surfactants", European Journal of Organic Chemistry, vol. 2003, No. 20, Oct. 1, 2003, pp. 4080-4086.
Bingwei Xin et al: "The Surfactant-Promoted Cross-Coupling Reactions of Arylboronic Acids with Carboxylic Anhydrides or Acyl Chlorides in Water", Synthesis, vol. 2007, No. 13, Jul. 1, 2007, pp. 1970-1978.
Bruce H. Lipshutz et al: "Olefin Cross-Metathesis Reactions at Room Temperature Using the Nonionic Amphiphile "PTS": Just Add Water +", Organic Letters, vol. 10, No. 7, Mar. 12, 2008, pp. 1325-1328.

* cited by examiner

*Primary Examiner* — Paul V Ward
(74) *Attorney, Agent, or Firm* — Francine F. Li

(57) ABSTRACT

The present invention is directed to reaction mixtures comprising a water-surfactant mixture and a co-solvent. This technology reduced the amount of organic solvents needed for performing chemical reactions. Furthermore, compared to reaction mixtures lacking the co-solvent, solvation of the reactants and products of the chemical reaction is greatly enhanced, leading to a significantly improved yield, purity, reproducibility and robustness.

38 Claims, No Drawings

REACTION MEDIUM CONTAINING WATER-SURFACTANT MIXTURE

FIELD OF THE INVENTION

The present invention is directed to improved reaction media which comprise a water-surfactant mixture and a co-solvent. Solvation of the reactants and products of the chemical reaction is greatly enhanced, leading to a significantly improved selectivity, yield and purity. The invention therefore provides a reaction mixture comprising a water-surfactant mixture and a co-solvent and a method of performing a chemical reaction using said reaction mixture.

BACKGROUND OF THE INVENTION

The identification of sustainable harmless solvent to be used for general purposes has been an area of focus by many chemistry groups globally in the last few decades. It became all the more important as not only the well-known ozone-depleting chlorinated solvents were flagged many years ago, but also when the reprotoxicity of such frequently used polar aprotic solvents as DMF, DMAC or NMP was made visible. To tackle this particular topic, a variety of more or less general strategies were followed by multiple groups around the world, developing neoteric solvents for example, which will have given rise to such solvents as the bio-based cyrene, or such ethers as CPME or the more powerful MeTHF, other harmless derivatives of problematic solvents developed directly by chemical producers, ionic liquids, or more sophisticated systems utilizing compressed gases or phase-transfer catalysis, switchable solvents, and fluorous systems. While punctual success stories can be found and have proven tremendous benefits at times, the generality is however lagging behind. This unfortunately did not yet lead to the required dramatic change in mindset. For example, time-critical experimentations continue relying on the most established undesirable DMF or NMP for example. This is all the more critical and relevant in the pharmaceutical industry where the physical properties of the target compounds routinely display limited solubility.

One approach towards the replacement of undesirable polar aprotic solvents was developed by Professor Lipshutz, disclosing his latest application on the benign-by-design surfactant chemistry. However, preliminary successes of this technology were combined with huge challenges, namely emulsion problems, oiling out, or precipitation resulting in sub-optimal conversions, and too limited generality.

Hence, there is a need in the art to provide a solvent system which ensures the expected productivity and reduces the amount of organic solvents, in particular environmentally harmful organic solvents, and at the same time can generally be used for industrial synthesis processes.

SUMMARY OF THE INVENTION

The present invention is based on the findings that in reaction mixtures using a surfactant-water mixture as reaction medium, small amounts of a co-solvent greatly improve stability/homogeneity of the reaction mixture via a pseudo-phase. Thereby, the chemical reaction is not disturbed by aggregation or oiling out of the reactants or products, as is the case in the absence of a co-solvent. This significantly improves the yield of the reaction and reduces unwanted side products. This was very surprising as it was generally assumed that chemical reactions in surfactant-water mixtures are feasible because the surfactant forms micelles which encapsulate and thereby solvate hydrophobic reactants and products. The addition of a co-solvent, however, was thought to disrupt the micelles and hence, destroy the positive effect of the surfactant micelles. In contrast thereto, the present inventors found that the presence of co-solvents greatly improves solvation of reactants and products in the surfactant-water mixture. Stable pseudo-phase/reaction mixtures are obtained, in particular in the form of colloidal suspensions. This allows the setup of reaction mixtures comprising the reactants in high concentrations. Since the invention enables homogeneous reaction mixtures also at high reactant concentrations, surfactant-water mixtures can now be used as reaction medium for chemical reactions at industrial scale or nanoliter scale. In these setups, high reactant concentrations are critical since the overall volume of the reaction mixture is restricted. In contrast to the present invention, without co-solvent the concentration of the reactants had to be lower in order to prevent aggregation or oiling out. For this reason, the use of the environmental-friendly and cost-saving surfactant-water mixtures as reaction medium was limited to lab-scale reactions, but was not feasible at industrial scale or for nanoscale applications.

In a first aspect, the present invention provides a reaction mixture comprising one or more reactants, optionally a catalyst, an organic solvent, and a surfactant-water mixture, wherein the reaction mixture comprises 0.1 to 50 volume equivalents of the organic solvent and 1 to 50 volume equivalents of the surfactant-water mixture per mass of the reactants or product, respectively.

In a second aspect, the present invention provides a method of performing a chemical reaction, comprising the steps of
  (a) providing a reaction mixture according to the first aspect of the invention, and
  (b) allowing the chemical reaction to proceed.

This includes embodiments wherein two or more different chemical reactions are performed subsequently without changing the reaction medium.

In a third aspect, the present invention provides a method of increasing the yield of a chemical reaction, and/or decreasing the amount of side products produced in a chemical reaction, and/or preventing phase separation during a chemical reaction, wherein the chemical reaction is performed in a surfactant-water mixture, comprising the steps of
  (a) providing a reaction mixture comprising one or more reactants, a catalyst, and a surfactant-water mixture, which additionally comprises an organic solvent, and
  (b) allowing the chemical reaction to proceed.

The above aspects can be combined. Other objects, features, advantages and aspects of the present invention will become apparent to those skilled in the art from the following description and appended claims. It should be understood, however, that the following description, appended claims, and specific examples, which indicate preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

The present invention provides, in a first aspect, a reaction mixture comprising one or more reactants, optionally a catalyst, an organic solvent, and a surfactant-water mixture, wherein the reaction mixture comprises 0.1 to 50 volume equivalents of the organic solvent and 1 to 50 volume equivalents of the surfactant-water mixture per mass of the reactants or product, respectively.

The inventive technology is suitable for all chemical reactions which can be performed in a medium comprising a surfactant-water mixture. It can in particular be used in organic chemistry, for example with at least partly hydrophobic compounds. Exemplary suitable chemical reactions include chemical reactions selected from the group consisting of cross-coupling reactions such as Suzuki cross-coupling, Suzuki-Miyaura cross-coupling, Sonogashira cross-coupling, Heck cross-coupling, Buchwald-Hartwig cross-coupling, Negishi cross-coupling, Stille cross-coupling, Miyaura borylation, Hiyama cross-couplings, Chan-Ma cross-coupling, and olefin metathesis; copper-mediated cross-couplings, nickel-mediated cross-couplings, nucleophilic substitutions such as nucleophilic aromatic substitution ($S_NAr$); electrophilic halogenation, aromatic and heteroaromatic halogenation; biocatalytic transformations; amidation; oxidation; reduction such as reduction of nitro groups, oxime groups, azide groups, nitrile groups and amide groups; nitrile and imine hydrolysis; hydrogenation and debenzylation. In certain embodiments, the chemical reaction is a Suzuki cross-coupling reaction. In other embodiments, the chemical reaction is a nucleophilic aromatic substitution. The reactants and the catalyst present in the reaction mixture are suitable for the specific chemical reaction. In particular, the reactants and the catalyst are specifically chosen so that the chemical reaction can be performed.

The surfactant in the surfactant-water mixture can be any surfactant. In particular, the surfactant should not interfere with the chemical reaction. In certain embodiments, the surfactant is a non-ionic surfactant. The surfactant generally is amphiphilic and comprises a hydrophilic part and a hydrophobic part. In specific embodiments, the surfactant is able to form micelles in the surfactant-water mixture.

In certain embodiments, the hydrophilic part of the surfactant comprises a polyalkylene glycol moiety, especially a polyethylene glycol moiety or a polypropylene glycol moiety. The polyalkylene moiety, especially the polyethylene glycol moiety, may have an average molecular weight in the range of about 100 to about 10,000 g/mol, especially in the range of about 300 to about 3,000 g/mol, in particular in the range of about 400 to about 2,000 g/mol. Certain examples of surfactants comprising a polyalkylene glycol moiety include tocopherol polyethylene glycol succinates (TPGS), in particular DL-α-tocopherol polyethylene glycol succinates such as TPGS-750-M, TPGS-1000, TPGS-1500, TPGS-400, TPGS-1100-M, TPGS-2000, TPGS-860-oleate, TPGS-PEG-PPG-PEG-1100 and TPGS-PPG-PEG-70-butyl, and DL-α-tocopherol polypropylene glycol succinates such as TPPG-1000 and TPPG-1000-butyl; Triton X-100; polyethylene glycol alkyl ethers such as Brij surfactants, in particular Brij 30, Brij 35, Brij 52, Brij 56, Brij 58, Brij 72, Brij 76, Brij 78, Brij 92, Brij 96, Brij 98, Cremophor A6, Cremophor A25 and Thesit; polyethylene glycol esters such as polyethylene glycol (15)-hydroxystearate (Solutol HS 15); polyethylene glycol sorbitan fatty acid esters, also known as polysorbates or Tween, such as polysorbate 20, polysorbate 21, polysorbate 40, polysorbate 60, polysorbate 61, polysorbate 65, polysorbate 80, polysorbate 81, polysorbate 85 and polysorbate 120; cholesteryl PEG succinates such as holesteryl PEG1000 succinate; (deoxy) cholic PEG such as colic PEG1000 and deoxy-cholic PEG1000; chromanol polyethylene glycol succinates such as Chrom-400 and Chrom-1000; b-sitosterol methoxyethyleneglycol succinate (Nok); and other derivatives of PEG such as C4-azo-PEG. In specific embodiments, the surfactant is a DL-α-tocopherol polyethylene glycol succinate, in particular TPGS-750-M.

Furthermore, also other surfactants can be used, including, for example, cetyltrimethylammonium bromide (CTAB); phase transfer surfactants (PTS) such as sodium deoxycholate; polyoxyethanyl ubiquinol sebacate (PQS) and functionalized PQS; and octanoic acid and other long alkyl chain acids, in particular C6-C20 alkyl chain acids.

The concentration of the surfactant in the surfactant-water mixture in particular is in the range of 0.1 to 10% (w/w). In certain embodiments, the concentration of the surfactant in the surfactant-water mixture is in the range of 0.5 to 5% (w/w), especially in the range of 0.8 to 4% (w/w), 1 to 3% (w/w) or 1.5 to 2.5% (w/w), such as about 2% (w/w). In specific embodiments, the concentration of the surfactant in the surfactant-water mixture is above its critical micellar concentration.

The organic solvent in the reaction mixture may be any organic solvent. Preferably, it shall not disturb or inhibit the chemical reaction and in particular shall increase the homogeneity of the reaction mixture. In certain embodiments, the organic solvent is water-miscible or partly water-miscible. The organic solvent especially is an aprotic organic solvent. Suitable examples of the organic solvent include acetone, tetrahydrofuran (THF) and derivatives thereof such as methyl tetrahydrofuran, pyridine, polyethylene glycol (PEG), polypropylene glycol (PPG), in particular PEG with an average molecular weight of about 100 g/mol to about 2000 g/mol such as PEG200, PEG600, PEG1000 and PEG2000, derivatives thereof such as mono- or dialkyl PEG, in particular mono- or dimethyl PEG, mono- or diethyl PEG and mono- or dipropyl PEG. Further examples include acetonitrile, dimethylformamide (DMF), dichloromethane (DCM), toluene, and alcohols such as a $C_{1-10}$ aliphatic alcohol, in particular 2-butyl alcohol. In certain embodiments, the organic solvent is not a base and/or does not act as base in the chemical reaction.

In specific embodiments, an organic solvent is used which increases the viscosity of the reaction mixture. For example, the viscosity of the reaction mixture containing the organic solvent is at least 1.25 cSt, especially at least 1.5 cSt, at least 1.75 cSt or at least 2.0 cSt. Suitable organic solvents which increase the viscosity of the reaction mixture include PEGs such as PEG200, PEG600 and PEG1000 (PEG with an average molecular weight of 200 g/mol, 600 g/mol and 1000 g/mol, respectively).

The catalyst in the reaction mixture may be any catalyst suitable for catalyzing the chemical reaction of the reactants into the desired product. Hence, the choice of the catalyst depends on the type of chemical reaction to be performed in the reaction mixture. In certain embodiments, the catalyst is a metal catalyst such as a copper catalyst, a ruthenium catalyst, a rhodium catalyst, a palladium catalyst, a nickel catalyst, a zinc catalyst, a gold catalyst, a manganese catalyst, an iron catalyst, and a cobalt catalyst. The catalyst may be present in form of a complex with appropriate ligands. Suitable catalysts and ligands are known in the art and can readily be selected by a person skilled in the art. The concentration of the catalyst in the reaction mixture is selected so that it is able to catalyze the desired chemical reaction. Suitable catalyst concentrations are for example 0.1 to 25 mol %, especially 1 to 20 mol %, 3 to 15 mol % or 5 to 10 mol %, with respect to the molar amount of one or more of the reactants. If the reaction mixture is for performing a chemical reaction which does not need a catalyst, the reaction mixture does not have to contain a catalyst.

The one or more reactants in the reaction mixture may be any reactants suitable for performing the chemical reaction. The reactants in particular depend on the type of chemical reaction which is to be performed in the reaction mixture. In certain embodiments, the reaction mixture comprises one reactant, two reactants or three reactants. In specific embodiments, at least one of the reactants is not water-miscible or only partly water-miscible. A reactant which is only partly water-miscible in particular is only miscible with water at a concentration of 20 g/l or less, especially 10 g/l or less or 5 g/l or less, at room temperature. Exemplary reactants include boronic acids, boronate esters, organosilanes, halides, acids and/or corresponding activated esters, amines, alcohols and alkenes. The reactants can be used in any concentration which is feasible for performing the chemical reaction. In particular, the reactants are used at high concentrations. For example, the concentration of at least one of the reactants, especially of all reactants, in the reaction mixture is at least 0.1 M, in particular at least 0.5 M, at least 1.0 M, at least 1.1 M, at least 1.2 M, at least 1.3 M, at least 1.5 M, at least 1.7 M or at least 2.0 M. In certain embodiments, the concentration of one or more of the reactants in the reaction mixture is above the saturation concentration of its solubility or miscibility in the surfactant-water mixture. In particular, it is at least about 5%, especially at least about 10%, at least about 20%, at least about 30% or at least about 50% above said saturation concentration. In these embodiments, solubility or miscibility of the reactants is provided by the organic solvent in the reaction mixture. The person skilled in the art is able to select suitable reactants and their concentrations.

In certain embodiments, the reaction mixture may additionally comprise a base. The presence of the additional base in the reaction mixture in particular depends on the type of chemical reaction which is to be performed in the reaction mixture. The base may be an organic base or an inorganic base. In particular, the base is at least partly water-soluble or at least partly water-miscible. Exemplary bases include trialkylamines such as triethylamine (TEA), N-methylmorpholine (NMM), 1,8-diazabicyclo[5.4.0]undec-7-ene (DBU), 1,4-diazabicyclo[2.2.2]octane (DABCO), $K_3PO_4$ and $Na_2CO_3$. The concentration of the base in the reaction mixture in particular is in the range of 0.5 to 10 molar equivalents of one of the reactants, especially in the range of 0.9 to 6, 1.0 to 5, 1.2 to 4 or 1.5 to 3.5 molar equivalents of one of the reactants. If the reaction mixture is for performing a chemical reaction which does not need a base, the reaction mixture does not have to contain a base.

The reaction mixture comprises 0.1 to 50 volume equivalents of the organic solvent and 1 to 50 volume equivalents of the surfactant-water mixture per mass of the reactants or product, respectively. The amount of the organic solvent and the amount of the surfactant-water mixture are defined in relation to the amount of the theoretical product or alternatively the reactants of the chemical reaction. In case the amount is defined based on the theoretical product, 1 volume equivalent equals the total weight of the theoretical product obtained by 100% conversion in the chemical reaction. The weight of the theoretical product is converted into volume using a theoretical density of 1 g/ml. Hence, if for example 1.5 kg product is calculated based on 100% conversion, 1 volume equals 1.5 l. In case the amount is defined based on the reactants, 1 volume equivalent equals the total weight of the reactants. The weight of the reactants is converted into volume using a theoretical density of 1 g/ml. Hence, if for example 1.5 kg reactants are used in the reaction mixture, 1 volume equals 1.5 l.

In certain embodiments, the amount of the organic solvent in the reaction mixture is at least 0.2 volume equivalents, in particular at least 0.4 volume equivalents, at least 0.6 volume equivalents, at least 0.8 volume equivalents, at least 1.0 volume equivalent, at least 1.5 volume equivalents, or at least 2.0 volume equivalents. In further embodiments, the amount of the organic solvent in the reaction mixture is at most 40 volume equivalents, in particular at most 30 volume equivalents, at most 25 volume equivalents, at most 20 volume equivalents, at most 15 volume equivalents, at most 12 volume equivalents, or at most 10 volume equivalents. In specific embodiments, the amount of the organic solvent in the reaction mixture is in the range of 0.4 to 25 volume equivalents, in particular 0.8 to 15 volume equivalents. In certain embodiments, the amount of the organic solvent in the reaction mixture is in the range of from 1% to 70%, in particular from 2% to 65%, from 3% to 60%, from 4% to 55% or from 5% to 50%.

In certain embodiments, the amount of the surfactant-water mixture in the reaction mixture is at least 1.5 volume equivalents, in particular at least 2.0 volume equivalents, at least 2.5 volume equivalents, at least 3.0 volume equivalents, at least 3.5 volume equivalents, at least 4.0 volume equivalents, or at least 5.0 volume equivalents. In further embodiments, the amount of the surfactant-water mixture in the reaction mixture is at most 45 volume equivalents, in particular at most 40 volume equivalents, at most 35 volume equivalents, at most 30 volume equivalents, at most 25 volume equivalents, at most 22 volume equivalents, or at most 20 volume equivalents. In specific embodiments, the amount of the surfactant-water mixture in the reaction mixture is in the range of 1.5 to 25 volume equivalents, in particular 2.0 to 20 volume equivalents. In certain embodiments, the amount of the surfactant-water mixture in the reaction mixture is in the range of from 30% to 98%, in particular from 35% to 95%, from 40% to 92%, from 45% to 90% or from 50% to 85%.

The amount of organic solvent and surfactant-water mixture together in particular may in certain embodiments not exceed 30 volumes, especially it is 25 volume equivalents or less, 20 volume equivalents or less or even 15 volume equivalents or less. In specific embodiments, the volume of the organic solvent in the reaction mixture is in the range of about 1% to about 200% of the volume of the surfactant-water mixture, in particular in the range of about 2% to about 150%, about 3% to about 120%, about 4% to about 110% or about 5% to about 100%.

The present technology is especially useful for applications where high reactant concentrations in the reaction mixture are desire, such as at very large scales or very small scales. In one embodiment, the reaction mixture is of industrial scale. It may for example have a volume of at least 1 l, in particular at least 10 l, at least 100 l, or at least 1000 l. In another embodiment, the reaction mixture is of microscale. It may for example have a volume of 10 ml or less, in particular 1 ml or less, 100 μl or less, 10 μl or less or 1 μl or less.

The reaction mixture is a charge or batch mixture for performing a chemical reaction. In certain embodiments the reaction mixture does not comprise any products of the reaction or comprises only residual amount of any products of the reaction. In other embodiments, it may also contain a significant amount of the product of the chemical reaction. In further embodiments, the reaction mixture does not comprise all reactants necessary to perform the chemical reaction. In particular, the reaction mixture comprises only one reactant. For example, in these embodiments one reactant may be added slowly to the reaction mixture and is directly consumed by the chemical reaction. In certain embodiments, the reaction mixture is a homogeneous mixture, especially a colloidal suspension. In particular, the reaction mixture does not contain aggregated or oiled out components such as reactant or product.

In a second aspect, the present invention provides a method of performing a chemical reaction, comprising the steps of
  (a) providing a reaction mixture as described herein, and
  (b) allowing the chemical reaction to proceed.

The reaction mixture especially comprises one or more reactants, optionally a catalyst, an organic solvent, and a surfactant-water mixture, wherein the reaction mixture comprises 0.1 to 50 volume equivalents of the organic solvent and 1 to 50 volume equivalents of the surfactant-water mixture per mass of the reactants or product, respectively. The reaction mixture in particular may exhibit any of the features, embodiments and examples described herein including combinations thereof.

The chemical reaction may be any chemical reactions which can be performed in a medium comprising a surfactant-water mixture. In particular organic chemical synthesis reactions can be performed, for example with at least partly hydrophobic compounds. Exemplary chemical reactions include chemical reactions selected from the group consisting of cross-coupling reactions such as Suzuki cross-coupling, Suzuki-Miyaura cross-coupling, Sonogashira cross-coupling, Heck cross-coupling, Buchwald-Hartwig cross-coupling, Negishi cross-coupling, Stille cross-coupling, Miyaura borylation, Hiyama cross-couplings, and olefin metathesis; copper-mediated cross-couplings, nickel-mediated cross-couplings, nucleophilic substitutions ($S_N 2$) such as nucleophilic aromatic substitution ($S_N Ar$); amidation; oxidation; reduction such as reduction of nitro groups, oxime groups, azide groups, nitrile groups and amide groups; hydrogenation and debenzylation. In certain embodiments, the chemical reaction is a Suzuki cross-coupling reaction. In other embodiments, the chemical reaction is a nucleophilic aromatic substitution. The reactants and the catalyst present in the reaction mixture are suitable for the specific chemical reaction. In particular, the reactants and the catalyst are specifically chosen so that the chemical reaction proceeds as desired.

In certain embodiments, the chemical reaction is allowed to proceed in step (b) at reaction conditions suitable for performing the chemical reaction. In particular, the reaction conditions include a temperature of 90° C. or less, especially 80° C. or less, 70° C. or less, 60° C. or less, 50° C. or less, 40° C. or less or 30° C. or less. For example, the chemical reaction may be allowed to proceed at about room temperature. In specific embodiments, the reaction mixture is agitated, in particular stirred, during the course of the chemical reaction.

For some chemical reactions, the order and speed of the addition of the various components of the reaction mixture is important. In some embodiments, one or more of the reactants are added slowly to the surfactant-water mixture, optionally comprising further components of the reaction mixture such as other reactants, the catalyst and the base. This in particular applies to reactants which have a low solubility in water. Slow addition in this respect refers for example to the addition of the reactant over a time period of at least 5 min, in particular at least 7 min, at least 10 min, at least 15 min, at least 20 min, at least 30 min, at least 45 min or at least 60 min. A low solubility in water in particular refers to a water solubility of 20 g/l or less, especially 10 g/l or less or 5 g/l or less at room temperature. In these embodiments, the organic solvent may be added to the surfactant-water mixture before addition of the reactant or it may be added together with the reactant. For example, the reactant may be mixed with or solved in the organic solvent and then added to the surfactant-water mixture.

The method of performing a chemical reaction also encompasses embodiments wherein two or more different chemical reactions are performed. In a further aspect, the present invention provides a method of subsequently performing two or more chemical reactions in one reaction vessel, comprising the steps of
  (a) providing a reaction mixture as described herein,
  (b) allowing a first chemical reaction to proceed,
  (c) adding one or more further reactants to the reaction mixture, and
  (d) allowing a second chemical reaction to proceed, wherein the product of the first chemical reaction is a reactant of the second chemical reaction.

One of the advantages of the present invention is that the reaction medium does not have to be exchanged between subsequent different chemical reactions. In specific embodiments, the reaction medium of the first chemical reaction is not removed between steps (b) and (d).

In certain embodiments, step (c) further comprises adding a catalyst to the reaction mixture. In further embodiments, step (c) further comprises adding an organic solvent to the reaction mixture. The catalyst and/or the organic solvent may be the same as already present in the reaction mixture, but in particular is a different catalyst and/or a different organic solvent.

The method may also comprise a third and optionally a fourth and optionally even any number of further chemical reactions. These additional chemical reactions are performed by repeating steps (c) and (d) the appropriate number of times, wherein in step (d) the respective chemical reaction (third, fourth, etc.) is allowed to proceed, and wherein the product of the respective previous chemical reaction (second, third, etc.) is a reactant. In specific embodiments, the reaction medium of the previous chemical reaction is not removed between two cycles of steps (c) and (d).

The methods of performing one or more chemical reactions may comprise the further step of isolating the product of the chemical reaction(s). In particular, this step is performed after completion of the (last) chemical reaction. The product is in particular separated from one or more, in particular essentially all of the other components of the reaction mixture. For example, the product is separated from one or more of remaining reactants, side products, catalysts, bases, organic solvents and/or surfactant-water mixture. Isolation of the product may be achieved by means and techniques known in the art, including for example evaporation of solvents, aggregation or crystallization and filtration, phase separation, chromatographic separation and others.

In certain embodiments, the reaction mixture is a homogeneous mixture throughout the entire chemical reaction(s), especially a colloidal suspension. "Throughout the entire chemical reaction" in this respect in particular means from the establishment of the final reaction mixture until the completion or termination of the chemical reaction.

The present invention improves the solubility of the reactants and products in the surfactant-water mixture and provides a stable and homogeneous reaction mixture.

thereby, the yield of the chemical reaction is increased and the amount of unwanted side products obtained by the chemical reaction is reduced. In view of this, the present invention in a further aspect provides a method of increasing the yield of a chemical reaction performed in a surfactant-water mixture, comprising the steps of (a) providing a reaction mixture comprising one or more reactants, optionally a catalyst, and a surfactant-water mixture, which additionally comprises an organic solvent, and (b) allowing the chemical reaction to proceed.

In a further aspect, the present invention provides a method of decreasing the amount of side products produced in a chemical reaction performed in a surfactant-water mixture, comprising the steps of (a) providing a reaction mixture comprising one or more reactants, optionally a catalyst, and a surfactant-water mixture, which additionally comprises an organic solvent, and (b) allowing the chemical reaction to proceed.

In a further aspect, the present invention provides a method of preventing phase separation during a chemical reaction performed in a surfactant-water mixture, comprising the steps of (a) providing a reaction mixture comprising one or more reactants, optionally a catalyst, and a surfactant-water mixture, which additionally comprises an organic solvent, and (b) allowing the chemical reaction to proceed.

The embodiments, features and examples described herein, including combinations thereof, for methods of performing a chemical reaction and reaction mixtures likewise apply to the methods of increasing the yield of, decreasing the amount of side products produced in, and preventing phase separation during a chemical reaction performed in a surfactant-water mixture and the reaction mixture provided in step (a) thereof, respectively. In particular, the reaction mixture provided in step (a) may comprise 1 volume of reactants, 0.1 to 50 volumes of the organic solvent and 1 to 50 volumes of the surfactant-water mixture.

The reaction mixture may be provided in step (a) by adding the different components to each other in any suitable order. For example, providing the reaction mixture in step (a) may include providing a surfactant-water mixture and adding to said surfactant-water mixture an organic solvent, optionally a catalyst, and one or more reactants.

The present invention also provides the use of an organic solvent for increasing the yield of, decreasing the amount of side products produced in, and/or preventing phase separation during a chemical reaction performed in a surfactant-water mixture.

The expression "comprise", as used herein, besides its literal meaning also includes and specifically refers to the expressions "consist essentially of" and "consist of". Thus, the expression "comprise" refers to embodiments wherein the subject-matter which "comprises" specifically listed elements may and/or indeed does encompass further elements as well as embodiments wherein the subject-matter which "comprises" specifically listed elements does not comprise further elements. Likewise, the expression "have" is to be understood as the expression "comprise", also including and specifically referring to the expressions "consist essentially of" and "consist of".

Numeric ranges described herein are inclusive of the numbers defining the range. The headings provided herein are not limitations of the various aspects or embodiments of this invention which can be read by reference to the specification as a whole. According to one embodiment, subject matter described herein as comprising certain steps in the case of methods or as comprising certain ingredients in the case of compositions refers to subject matter consisting of the respective steps or ingredients. It is preferred to select and combine specific aspects and embodiments described herein and the specific subject-matter arising from a respective combination of specific embodiments also belongs to the present disclosure.

EXAMPLES

Example 1

Synthesis of N-[4-(chlorodifluoromethoxy)phenyl]-6-[(3R)-3-hydroxypyrrolidin-1-yl]-5-[1-(oxan-2-yl)-1H-pyrazol-5-yl]pyridine-3-carboxamide via Amidation Reaction 4-methylmorpholine (NMM; 3 eq, 0.85 wt), the carboxylic acid (1 eq, 1 wt)), 1-hydroxybenzotriazole hydrate (HOBT) (1.2 eq, 0.47 wt) and TPGS-750M aqueous solution 2% wt (15 wt) were charged into the vessel and stirred at RT until clear solution is formed. The solution was warmed to 35° C. A solution of 1-ethyl-3-(3-dimethylaminopropyl) carbodiimide (EDCI) (1.7 eq, 0.94 wt), the amine (1.2 eq, 0.66 wt), PEG200 (3.8 wt) in water (0.33 wt) was added sequentially over 3 h and stirred for another 16 h. Over the course of the reaction, the desired product precipitated out of the mixture. The suspension is filtered and washed with two portion of $H_2O$/Methanol 4:1

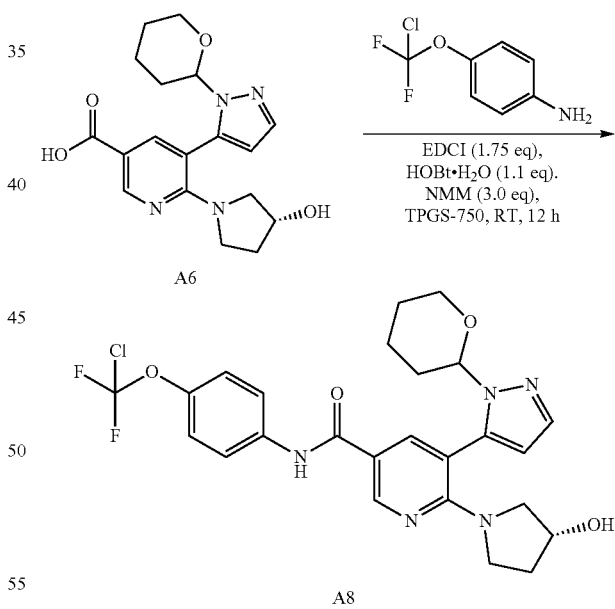

mixture (4 wt). The cake is dried under vacuum. A typical yield of 90% is obtained.

The absence of co-solvent such as PEG-200 results in an oiling out of the amine as it is added to the mixture and in non-reproducible results.

The same chemical reaction performed in Acetonitrile as only solvent had to be performed at 50° C. instead of room temperature and resulted in a yield of only 77%. Furthermore, 12% of the unwanted dimer side product was obtained.

Example 2

Synthesis of methyl 3-amino-6-[3-(trifluoromethyl)pyridin-2-yl]pyrazine-2-carboxylate via Suzuki Cross-Coupling Reaction 10.0 g (44.2 mmol) of 2-bromo-3-(trifluoromethyl)pyridine and 18.5 g (53.1 mmol/1.2 eq.) of methyl 3-amino-6-(4,4,5,5-tetramethyl-1,3,2-dioxaborolan-2-yl)pyrazine-2-carboxylate was provided in a reaction mixture comprising 3.0 mol % [1,1'-bis(di-tert-butylphosphino)ferrocene]dichloropalladium(II) ($PdCl_2$(dtbpf)) and 2.0 eq. triethylamine (TEA) in 150 ml (15V) 2% TPGS-750-M in water and 30 ml (2V) tetrahydrofuran (THF). The reaction mixture formed a stable emulsion and the reaction was allowed to proceed overnight at room temperature under stirring. The product 3-amino-6-[3-(trifluoromethyl)pyridin-2-yl]pyrazine-2-carboxylate was obtained with a yield of more

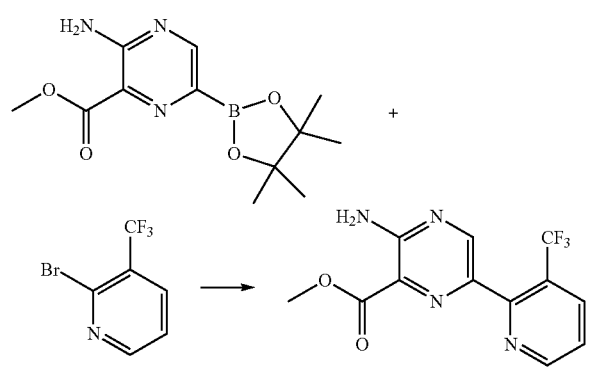

than 80%.

The same reaction using 10V 2% TPGS-750-M in water and 10V acetone as solvents, wherein 1.05 eq. methyl 3-amino-6-(4,4,5,5-tetramethyl-1,3,2-dioxaborolan-2-yl)pyrazine-2-carboxylate was added in 4 portions, resulted in more than 99% yield after 1 h at room temperature.

Example 3

Synthesis of 2-amino-4-((2S,4S)-2-(6-fluoro-5-(2-methoxypyrimidin-5-yl)-4-oxo-3-phenyl-3,4-dihydroquinazolin-2-yl)-4-hydroxpyrrolidin-1-yl)-6-methylpyrimidine-5-carbonitrile via Suzuki Cross-Coupling Reaction and Aromatic Nucleophilic Substitution Reaction In this example, two different synthesis reactions were performed subsequently in one reaction vessel without exchange of the reaction medium.

5.0 g (11.3 mmol) of 5-bromo-6-fluoro-2-((2S,4S)-4-hydroxypyrrolidin-2-yl-3-phenylquinazolin-4(3H)-one hydrochloride and 1.9 g (12.5 mmol/1.1 eq.) of (2-methoxypyrimidin-5-yl)boronic acid was provided in a reaction mixture comprising 5.0 mol % $PdCl_2$(dtbpf) and 3.0 eq. NMM in 40 ml (8V) 2% TPGS-750-M in water and 20 ml (4V) THF. The reaction mixture formed a stable emulsion and the reaction was allowed to proceed for 16 h at 50° C. under stirring. Then 1.7 g (10.2 mmol/0.9 eq.) of 2-amino-4-chloro-6-methylpyrimidine-5-carbonitrile in 10 ml (2V) THF were added to the reaction mixture. After 18 h at room temperature the product 2-amino-4-((2S,4S)-2-(6-fluoro-5-(2-methoxypyrimidin-5-yl)-4-oxo-3-phenyl-3,4-dihydroquinazolin-2-yl)-4-hydroxpyrrolidin-1-yl)-6-methylpyrimidine-5-carbonitrile was obtained.

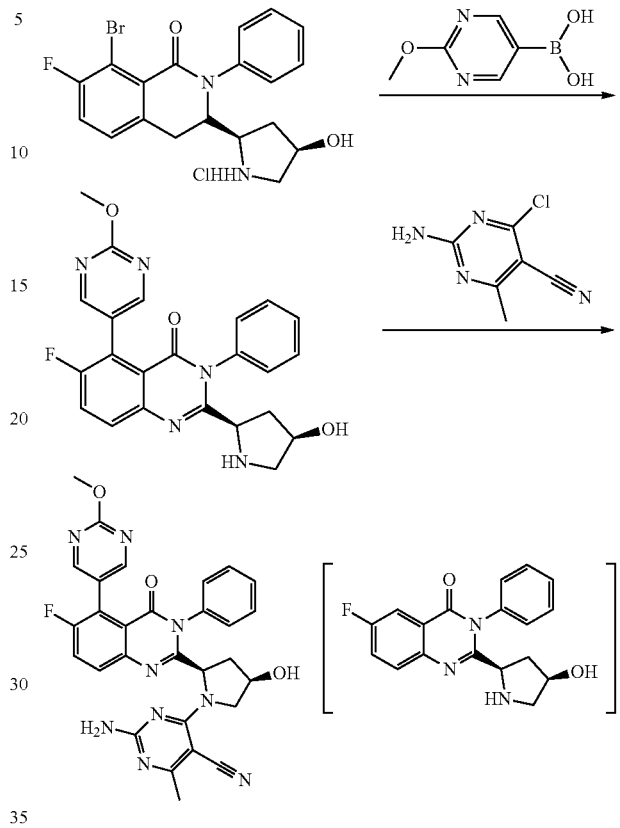

The same reaction performed in conventional organic solvent (e.g. N-methylpyrrolidone) resulted in about 30% side product (structure in bracket) of the Suzuki cross-coupling reaction. This could be reduced to 3% with the use of 2% TPGS-750-M in water as solvent and THF as co-solvent.

Example 4

Synthesis of tert-butyl (3R,4S,5S)-4-((S)-2-(((benzyloxy)carbony)amino)-N,3-dimethylbutanamido)-3-methoxy-5-methylheptanoate via Amidation Reaction 108.0 g (429.8 mmol) of ((benzyloxy)carbonyl)-L-valine and 139.8 g (472.4 mmol/1.1 eq.) of tent-butyl (3R,4S,5S)-3-methoxy-5-methyl-4-(methylamino)heptanoate hydrochloride was provided in a reaction mixture comprising 1.5 eq. 4-(4,6-dimethoxy-1,3,5-triazin-2-yl)-4-methylmorpholinium chloride (DMTMM) and 2.0 eq. NMM in 1080 ml (10 V) 2% TPGS-750-M in water and 216 ml (2V) THF. The reaction mixture formed a stable emulsion and the reaction was allowed to proceed for 18 h at room temperature under stirring. The product [tent-butyl (3R,4S,5S)-4-((S)-2-(((benzyloxy)carbonyl)amino)-N,3-dimethylbutanamido)-3-methoxy-5-methylheptanoate] was obtained with a yield of 88%.

The absence of co-solvent such as THF resulted in the formation of oil balls and the yield was reduced to 66%.

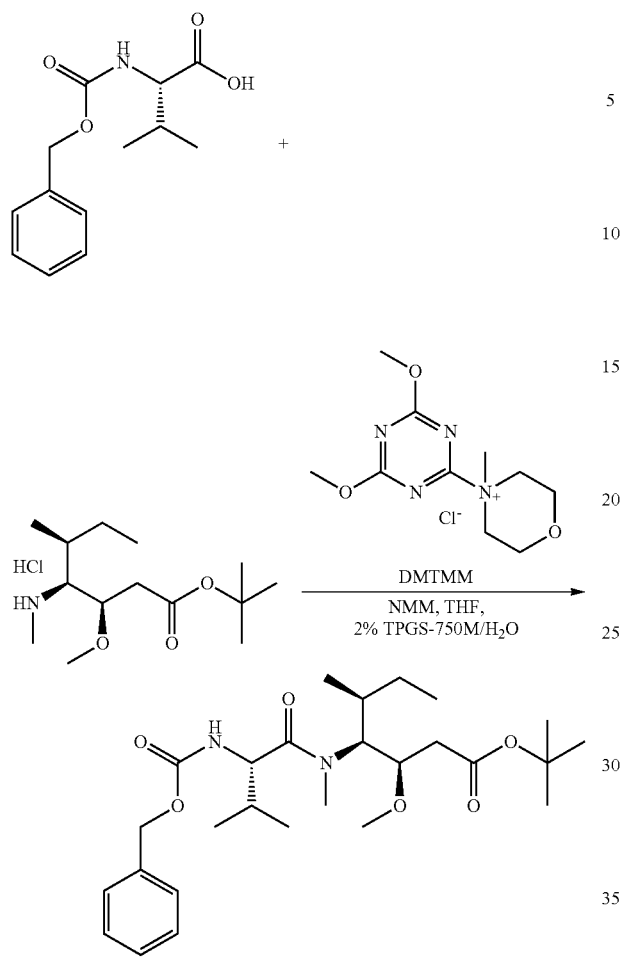

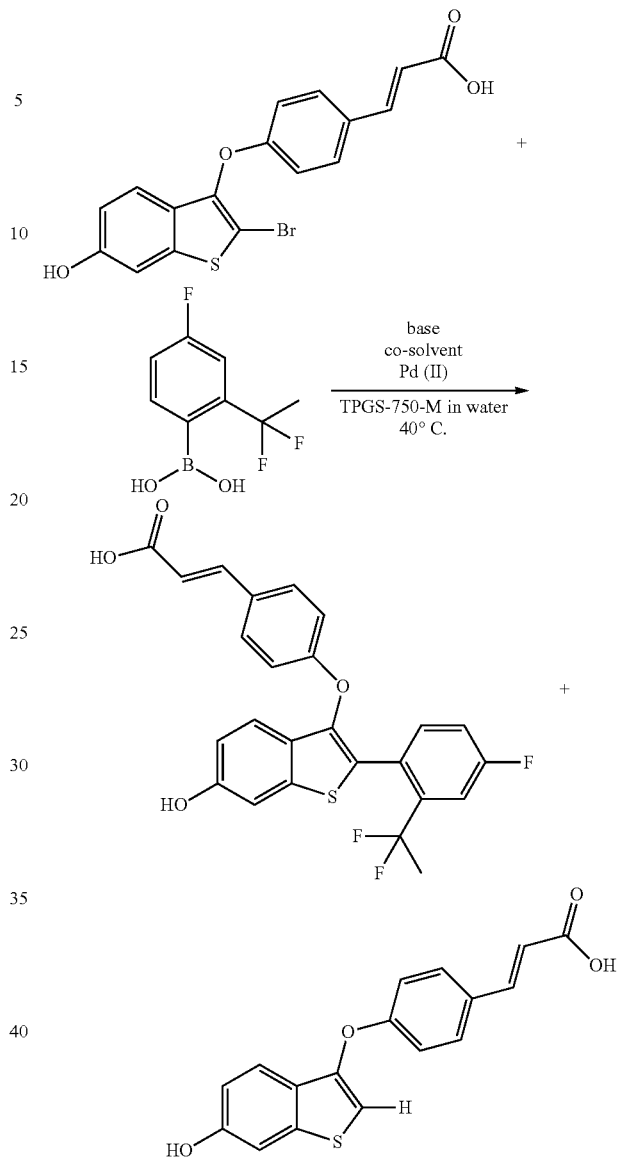

Example 5

Synthesis of (2E)-3-[4-({2-[2-(1,1-difluoroethyl)-4-fluorophenyl]-6-hydroxy-1-benzothiophen-3-yl}oxy)phenyl]prop-2-enoic acid via Suzuki Cross-Coupling Reaction Into a degassed flask was added the boronic acid (0.3 eq, 0.16 wt) and acetone (0.4 wt) to give a light yellow solution at RT. TPGS-750M aqueous solution 2% wt (20 wt) was then added followed by LiBr (0.44 wt). The solution was degassed for 5 min and the catalyst $PdCl_2$(dtbpf) (3 mol %, 0.05 wt) was added. The mixture was heating to 40° for 15 min. The bromide derivative (1 eq, 1 wt) was added and the mixture was stirred for 15 min. The rest of the boronic acid (1.0 eq, 0.52 wt) dissolved in acetone (1.6 wt) was added dropwise over 5 min. The mixture was stirred for 30 min at 40° C. and $K_3PO_4$ (3 eq, 1.6 wt) was added as a solid. The resulting solution was stirred for 3 h. After cooling down to RT, MeTHF (20 wt) was added and the biphasic mixture was stirred for 30 min. Concentrated HCl was added dropwise until the pH reach a value of about 2. The aqueous layer was separated and extracted back with MeTHF (4 wt). The combined organic layers were filtered over celite and azeotropically dried to give the desired compound as an oil (yield typical >70%).

The absence of co-solvent such as acetone resulted in an oiling out of the product or gummy material. Non-reproducible results were obtained as well as non-suitable physical properties of the mixture for large scale production. The quality of the material produced was also highly impacted.

In comparison with the same reaction performed in standard organic solvent, the generation of the desbromo side product was reduced from 8% to 0.7%.

Example 6

Reduction of the Nitro Group of 4-nitrochlorobenzene 78 mg of 4-nitrochlorobenzene was provided in a reaction mixture comprising Fe nanoparticles with 80 ppm Pd, and 1.5 eq. $NaBH_4$ in 500 μl (~6 V) 2% TPGS-750-M in water and 156 μl (2V) THF. The reaction mixture formed a stable emulsion and the reaction was allowed to proceed for 18 h at room temperature under stirring. The product 4-chloroaniline was obtained with a yield of 100%. The same nitro reduction reaction was done with 2-methyl-THF, toluene and PEG200 as co-solvent instead of THF.

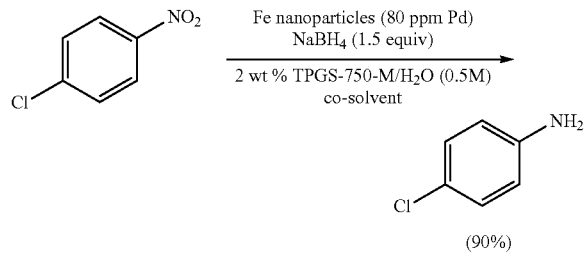

Example 7

Synthesis of 5-chloro-2,3-dimethyl-2,4'-bipyridine via Suzuki Cross-Coupling Reaction 2.8 g (20.4 mmol) of (2-methylpyridin-4-yl)boronic acid and 6.3 g (30.6 mol/1.5 eq.) of 2-bromo-5-chloro-3-methylpyridine was provided in a reaction mixture comprising 5.0 mol % $PdCl_2$(dtbpf) and 2.0 eq. TEA in 28 ml (10 V) 2% TPGS-750-M in water and 5.6 ml (2V) THF. The reaction mixture formed a stable emulsion and the reaction was allowed to proceed for 18 h at 40° C. under stirring. The product 5-chloro-2',3-dimethyl-2,4'-bipyridine was obtained with a yield of about 100%.

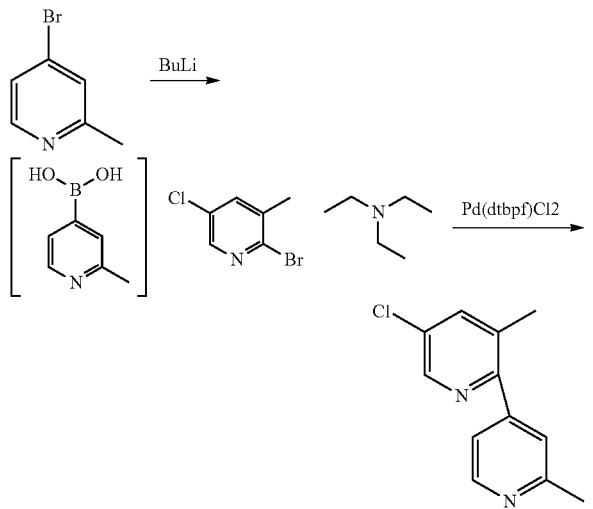

The same reaction using 1V acetone as co-solvents, wherein 1.5 eq. or 1.1 eq. 2-bromo-5-chloro-3-methylpyridine was added, also resulted in about 100% yield after 4 h at room temperature.

Example 8

Synthesis of 8-bromo-N-4((5-fluoro-2,3-dihydrobenzofuran-4-yl)methyl)-[1,2,4]triazolo[4,3-c]pyrimidin-5-amine via Aromatic Nucleophilic Substitution Reaction Compound (5-fluoro-2,3-dihydrobenzofuran-4-yl)methanamine hydrochloride (5 g, 1.0 eq.) and 8-bromo-5-(methylthio)-[1,2,4]triazolo[4,3-c]pyrimidine (6.9 g, 1.2 eq.) were dissolved in 2% TPGS-750-M in water (35 ml), pyridine (10 ml) and 1,8-diazabicyclo[5.4.0]undec-7-ene (DBU) (3.7 g). The mixture was stirred at 48° C. over 60 h. Ethanol (120 ml) was added into above reaction mixture, stirred 1 h at 60° C. and then 1 h at 25° C. The precipitate was collected by filtration. The reaction yield was 55% (based on (5-fluoro-2,3-dihydrobenzofuran-4-yl)methanamine hydrochloride) at a purity of 98.7%, compared to a yield of 30% (based on (5-fluoro-2,3-dihydrobenzofuran-4-yl)methanamine hydrochloride) at the same purity for the same reaction performed in common organic solvents.

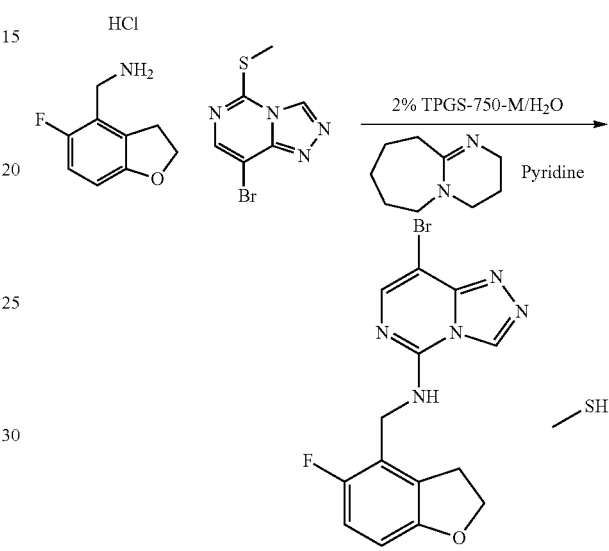

Example 9

Synthesis of 3-bromo-5-((1S,3S,4S)-4-((tert-butyldimethylsilyl)oxy)-3-fluorocyclohexyl)pyrazin-2-amine via Bromination 1.6 g (5.0 mmol) of 5-((1S,3S,4S)-4-((tert-butyldimethylsilyl)oxy)-3-fluorocyclohexyl)pyrazin-2-amine was provided in a reaction mixture comprising 1.4 eq. N-bromosuccinimide in 20 ml (12V) 2% TPGS-750-M in water and 10 mL acetone (6V). The reaction mixture formed a stable emulsion and the reaction was allowed to proceed for 0.5 h at 25° C. under stirring. Then the product 3-bromo-5-((1S,3S,4S)-4-((tert-butyldimethylsilyl)oxy)-3-fluorocyclohexyl)pyrazin-2-amine was obtained.

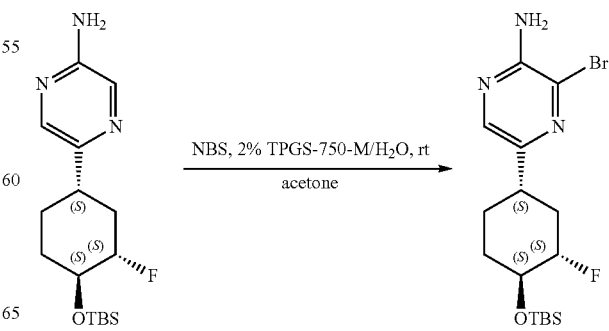

The invention claimed is:

1. A reaction mixture comprising one or more reactants, a catalyst, an organic solvent, and a surfactant-water mixture, wherein the reaction mixture comprises 0.1 to 50 volume equivalents of the organic solvent, and 1 to 50 volume equivalents of the surfactant-water mixture per mass of the reactants or product, respectively, wherein the surfactant is selected from the group consisting of (DL-α-) tocopherol polyethylene glycol succinate (TPGS), polyethylene glycol ester, Tween, phase transfer surfactants (PTS), polyoxyethanyl ubiquinol sebacate (PQS) and functionalized PQS, polyethylene glycol (PEG), octanoic acid, and b-sitosterol methoxyethyleneglycol succinate (Nok).

2. The reaction mixture according to claim 1, wherein the reaction mixture is for performing a chemical reaction selected from the group consisting of a cross-coupling reaction, wherein the cross-coupling reaction is a Suzuki cross-coupling, Suzuki-Miyaura cross-coupling, Sonogashira cross-coupling, Heck cross-coupling, Buchwald-Hartwig cross-coupling, Negishi cross-coupling, Stille cross-coupling, Miyaura borylation, Hiyama cross-coupling, Chan-Ma cross-coupling, olefin metathesis; copper-mediated cross-coupling, and nickel-mediated cross-coupling; a nucleophilic substitution, wherein the nucleophilic substitution is a nucleophilic aromatic substitution ($S_NAr$); electrophilic halogenation; aromatic and heteroaromatic halogenation; biocatalytic transformations; amidation; oxidation; reduction, wherein the reduction is a reduction of a nitro group, oxime group, azide group, nitrile groups and amide groups; nitrile and imine hydrolysis; hydrogenation; and debenzylation.

3. The reaction mixture according to claim 1, wherein the surfactant is a non-ionic surfactant.

4. The reaction mixture according to claim 1, wherein the surfactant comprises a hydrophilic part and a hydrophobic part, and wherein the hydrophilic part of the surfactant comprises a polyethylene glycol moiety.

5. The reaction mixture according to claim 1, wherein the surfactant is a (DL-α-) tocopherol polyethylene glycol succinate (TPGS) polyethylene glycol ester, Tween, phase transfer surfactants (PTS), and polyethylene glycol (PEG).

6. The reaction mixture according to claim 1, wherein the concentration of the surfactant in the surfactant-water mixture is above its critical micellar concentration.

7. The reaction mixture according to claim 1, wherein the concentration of the surfactant in the surfactant-water mixture is 0.5 to 5% (w/w).

8. The reaction mixture according to claim 1, wherein the organic solvent is water-miscible.

9. The reaction mixture according to claim 1, wherein the organic solvent is an aprotic organic solvent.

10. The reaction mixture according to claim 1, wherein the organic solvent is selected from the group consisting of acetone, tetrahydrofuran (THF), polyethylene glycol (PEG) (e.g. PEG200, PEG600, PEG1000), mono- or dialkyl PEG such as mono- or dimethyl PEG, mono- or diethyl PEG and mono- or dipropyl PEG, polypropylene glycol (PPG), mono- or dialkyl PPG, methyl tetrahydrofuran, and pyridine.

11. The reaction mixture according to claim 1, wherein the organic solvent is not a base and/or does not act as base in the reaction.

12. The reaction mixture according to claim 1, wherein reaction mixture comprises 0.4 to 25 volume equivalents of the organic solvent and 1.5 to 25 volume equivalents of the surfactant-water mixture per mass of the reactants or product, respectively.

13. The reaction mixture according to claim 1, wherein reaction mixture comprises 0.8 to 15 volume equivalents of the organic solvent and 2 to 20 volume equivalents of the surfactant-water mixture per mass of the reactants or product, respectively.

14. The reaction mixture according to claim 1, wherein the amount of organic solvent and surfactant-water mixture together does not exceed 20 volume, preferably 15 volume equivalents.

15. The reaction mixture according to claim 1, wherein the amount of the organic solvent in the reaction mixture is in the range of from 3% to 60%, and/or the amount of the surfactant-water mixture in the reaction mixture is in the range of from 35% to 95%.

16. The reaction mixture according to claim 1, wherein the reaction mixture does not comprise any products of the reaction or comprises only residual amount of any products of the reaction.

17. The reaction mixture according to claim 1, wherein the catalyst is selected from the group consisting of copper catalysts, ruthenium catalysts, rhodium catalysts, palladium catalysts, nickel catalysts, zinc catalysts, gold catalysts, manganese catalysts, iron catalysts and cobalt catalysts, and complexes thereof with appropriate ligands.

18. The reaction mixture according to claim 1, wherein the reaction mixture comprising one reactant or two reactants.

19. The reaction mixture according to claim 1, wherein one of the reactants is selected from the group consisting of boronic acids, boronate esters, organosilanes, halides, acids and/or corresponding activated esters, amines, alcohols, and alkenes.

20. The reaction mixture according to claim 1, wherein at least one of the reactants is present in the reaction mixture in a concentration of at least 1.5 M.

21. The reaction mixture according to claim 1, wherein the reaction mixture further comprises a base.

22. The reaction mixture according to claim 21, wherein the base is selected from the group consisting of trialkylamine such as triethylamine (TEA), N-methylmorpholine (NMM), 1,8-diazabicyclo[5.4.0]undec-7-ene (DBU), 1,4-diazabicyclo[2.2.2]octane (DABCO), and inorganic bases such as for example, but not limited to, $K_3PO_4$ and $Na_2CO_3$.

23. The reaction mixture according to claim 5, wherein the tocopherol polyethylene glycol succinate (TPGS) is TPGS-750-M, TPGS-1000 or TPGS-1500; the polyethylene glycol ester is polyethylene glycol (15)-hydroxystearate (Solutol HS 15); the Tween is Tween 20 or Tween 80; the phase transfer surfactant (PTS) is sodium deoxycholate; and the polyethylene glycol is C4-azo-PEG.

24. The reaction mixture according to claim 1, wherein the volume of the reaction mixture is at least 10 l.

25. The reaction mixture according to claim 1, wherein the surfactant is TPGS-750-M.

26. The reaction mixture according to claim 1, wherein the volume of the reaction mixture is 1 ml or less.

27. The reaction mixture according to claim 1, wherein the reaction mixture is a homogeneous mixture.

28. The reaction mixture according to claim 1, wherein the reaction mixture is a colloidal suspension.

29. A method of performing a chemical reaction, comprising the steps of
   (a) providing a reaction mixture according to claim 1, and
   (b) allowing the chemical reaction to proceed.

30. The method according to claim 29, wherein the reaction is performed at a temperature of 80° C. or less.

31. The method according to claim 29, wherein the reaction is performed at a temperature of 60° C. or less.

32. The method according to claim 29, wherein the reaction mixture is for performing a chemical reaction selected from the group consisting of a cross-coupling reaction, wherein the cross-coupling reaction is a Suzuki cross-coupling, Suzuki-Miyaura cross-coupling, Sonogashira cross-coupling, Heck cross-coupling, Buchwald-Hartwig cross-coupling, Negishi cross-coupling, Stille cross-coupling, Miyaura borylation, Hiyama cross-couplings, Chan-Ma cross-coupling, olefin metathesis;, copper-mediated cross-coupling, and nickel-mediated cross-coupling; a nucleophilic substitution, wherein the nucleophilic substitution is a nucleophilic aromatic substitution ($S_NAr$); electrophilic halogenation; aromatic and heteroaromatic halogenation; biocatalytic transformations;
  amidation; oxidation; reduction, wherein the reduction is a reduction of a nitro group, oxime group, azide group, nitrile group and amide group; nitrile and imine hydrolysis; hydrogenation;
  and debenzylation.

33. A method of subsequently performing two or more chemical reactions in one reaction vessel, comprising the steps of
  (a) providing a reaction mixture according to claim 1,
  (b) allowing a first chemical reaction to proceed,
  (c) adding one or more further reactants to the reaction mixture, and
  (d) allowing a second chemical reaction to proceed, wherein the product of the first chemical reaction is a reactant of the second chemical reaction.

34. The method according to claim 33, wherein step (c) further comprises adding a catalyst and/or an organic solvent to the reaction mixture.

35. The method according to claim 33, wherein the reaction medium of the first chemical reaction is not removed between steps (b) and (d).

36. The method according to claim 29, further comprising the step of isolating the product of the chemical reaction(s).

37. The method according to claim 29, wherein the reaction mixture is a homogeneous mixture throughout the entire chemical reaction(s).

38. The method according to claim 29, wherein the reaction mixture is a colloidal suspension throughout the entire chemical reaction(s).

* * * * *